United States Patent [19]

Hoelderich et al.

[11] Patent Number: 5,081,247

[45] Date of Patent: Jan. 14, 1992

[54] PREPARATION OF PYRIDINES

[75] Inventors: Wolfgang Hoelderich, Frankenthal; Norbert Goetz, Worms, both of Fed. Rep. of Germany

[73] Assignee: BASF Aktiengesellschaft, Ludwigshafen, Fed. Rep. of Germany

[21] Appl. No.: 449,401

[22] Filed: Dec. 19, 1989

Related U.S. Application Data

[63] Continuation of Ser. No. 184,961, Apr. 22, 1988, abandoned.

[30] Foreign Application Priority Data

May 5, 1987 [DE] Fed. Rep. of Germany ....... 3714857

[51] Int. Cl.$^5$ .................. C07D 213/12; C07D 213/14
[52] U.S. Cl. ..................................... 546/250; 546/251
[58] Field of Search ............................... 546/250, 251

[56] References Cited

U.S. PATENT DOCUMENTS

| | | | |
|---|---|---|---|
| 2,528,978 | 11/1950 | Smith et al. | 546/251 |
| 2,741,618 | 4/1956 | Young | 546/251 |
| 3,492,305 | 1/1970 | Colchester | 546/251 |
| 4,220,783 | 9/1980 | Chang et al. | 546/251 |
| 4,384,120 | 5/1983 | Merger et al. | 546/251 |
| 4,675,410 | 6/1987 | Feitler et al. | 546/251 |

FOREIGN PATENT DOCUMENTS

| | | | |
|---|---|---|---|
| 0131887 | 1/1985 | European Pat. Off. | 546/251 |
| 2038533 | 2/1971 | Fed. Rep. of Germany | 546/251 |
| 1695242 | 1/1972 | Fed. Rep. of Germany | 546/251 |
| 726378 | 3/1955 | United Kingdom | 546/251 |
| 1087279 | 10/1967 | United Kingdom | 546/251 |

OTHER PUBLICATIONS

Ullmanns Encyklopadie der technischen Chemie, vol. 19, p. 593.

*Primary Examiner*—Alan L. Rotman
*Attorney, Agent, or Firm*—Keil & Weinkauf

[57] ABSTRACT

Pyridines of the formula

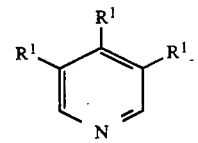

(I)

where the individual radicals $R^1$ may be identical or different and are each hydrogen or an aliphatic radical are prepared by reacting a) a 2-alkoxy-2,3-dihydro-4H-pyran of the formula

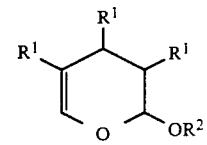

(II)

or b) a glutaraldehyde of the formula

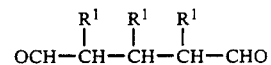

(III)

where $R^1$ has the abovementioned meansings and $R^2$ is an aliphatic radical, with ammonia in the presence of an acidic, solid catalyst.

16 Claims, No Drawings

PREPARATION OF PYRIDINES

This application is a continuation of application Ser. No. 184,961, filed on Apr. 22, 1988, now abandoned.

The present invention relates to a process for the preparation of pyridines by converting a 2-alkoxy-2,3-dihydro-4H-pyran or a glutaraldehyde in the presence of an acidic, solid catalyst (heterogeneous catalyst).

British Patent 1,102,261 describes a process for the preparation of pyridines by reacting glutaraldehyde, substituted glutaraldehyde or a 2-alkoxy-2,3-dihydro-4H-pyran with ammonia or an ammonium salt in the presence of oxygen and a copper(II) or iron(III) halide. Pyridine selectivities of 44%, based on the dialdehyde used, are achieved. In addition to the moderate yield, the process has the disadvantage that 44 mol %, based on aldehyde, of copper(II) chloride and 542 mol %, based on aldehyde, of ammonium chloride are used in the reaction, leading to byproducts (chloropyridines), which makes it difficult to purify the unhalogenated pyridine.

European Patent 57,366 discloses that the reaction with ammonium nitrate can be carried out in the presence of an aliphatic carboxylic acid. This process has the disadvantage that the ammonia required for the reaction has to be used in the form of ammonium nitrate, the reaction must be carried out in the presence of the corrosive carboxylic acids, and isolation of the desired product from the reaction mixture necessitates a more expensive procedure. Furthermore, the use of nitric acid as a cocatalyst is just as much a disadvantage as the formation of the nitrous acid, since safety measures have to be taken where oxides of nitrogen occur.

It is also known that pyridines can be prepared from 2-alkoxy-3,4-dihydropyrans over oxidation catalysts, for example Mo Bi P oxides (JA 7244747-R) or over noble metal-doped $Al_2O_3$ or $SiO_2$ (GB 1 087 279), in the presence of water and oxygen. The use of water and oxygen, which is necessary for this purpose, requires a larger amount of energy (heating and cooling the water) during isolation of the desired product and more complicated safety measures.

We have found that pyridines of the formula (I)

$$\text{(I)} \quad R^1 \text{-pyridine ring with } R^1 \text{ substituents}$$

where the individual radicals $R^1$ may be identical or different and are each hydrogen or an aliphatic radical, are obtained, by a procedure which avoids these disadvantages, if ammonia is reacted with a) a 2-alkoxy-2,3-dihydro-4H-pyran of the formula (II)

$$\text{(II)} \quad \text{dihydropyran with } R^1 \text{ and } OR^2$$

or b) a glutaraldehyde of the formula (III)

$$\text{(III)} \quad OCH-CHR^1-CHR^1-CHR^1-CHO$$

where $R^1$ has the abovementioned meanings and $R^2$ is an aliphatic radical, in the presence of an acidic, solid catalyst.

It is also possible in principle for the alkoxy group to be in position 2 or 3 instead of position 1.

Where 2,3-dihydro-2-methoxy-4H-pyran or glutardialdehyde is used, the reaction can be represented by the following equations:

$$\text{2-methoxy-dihydropyran} + NH_3 \xrightarrow{-H_2O, -CH_3OH, -H_2} \text{pyridine}$$

$$OCH-(CH_2)_3-CHO + NH_3 \xrightarrow{-2H_2O, -H_2} \text{pyridine}$$

Compared with the known processes, the process according to the invention gives pyridines by a simpler method and in better space-time yield, yield and purity. Surprisingly, it is possible to dispense with oxygen and other oxidizing agents, such as salts of trivalent iron or manganese or divalent copper and with carboxylic acids, resulting in substantially simpler working up and isolation of the reaction product. The novel process is furthermore environmentally compatible since it requires no heavy metal salts which pollute the wastewater, and is carried out without corrosive starting materials.

The starting materials (II) and (III) can be reacted with ammonia in a stoichiometric amount or in excess. Preferred starting materials II and III, and accordingly preferred end products I, are those in whose formulae the individual radicals $R^1$ and $R^2$ may be identical or different and are each alkyl of 1 to 8 carbon atoms, and $R^1$ may furthermore be hydrogen. The abovementioned radicals may furthermore be substituted by groups which are inert under the reaction conditions, e.g. alkyl, alkoxy or carboxyl, each of 1 to 4 carbon atoms.

Examples of suitable starting materials (II) are 2,3-dihydro-2-methoxy-4H-pyrans which are monosubstituted in the 3-, 4- or 5-position or disubstituted in the 3,4-, 4,5- or 3,5-position by identical or different radicals or trisubstituted in the 3-, 4- and 5-position by identical or different radicals, the substituents being methyl, ethyl, propyl, isopropyl, butyl, isobutyl, sec-butyl or tert-butyl; and 2-ethoxy-, 2-propoxy-, 2-isopropoxy-, 2-butoxy-, 2-isobutoxy-, 2-sec-butoxy- and 2-tert-butoxy-4H-pyrans which are unsubstituted or homologously substituted by the abovementioned substituents.

Examples of suitable starting materials (III) are glutaraldehydes which are monosubstituted in the 2-, 3- or 4-position or disubstituted in the 2,3-, 3,4-or 2,4-position by identical or different radicals or trisubstituted in the 2,3,4-position by identical or different radicals, the substituents being methyl, ethyl, propyl, isopropyl, butyl, isobutyl, sec-butyl or tert-butyl; and unsubstituted glutaraldehyde.

Acidic zeolite catalysts are used as acidic, solid catalysts (heterogeneous catalysts) for the process according to the invention. Zeolites are crystalline aluminosilicates which have a highly ordered structure with a rigid 3-dimensional network of $SiO_4$ and $AlO_4$ tetrahedra which are bonded by common oxygen atoms. The ratio of Si and Al atoms to oxygen is 1:2 (cf. Ullmanns Encyclopädie der technischen Chemie, 4th Edition, Volume 24, page 575 (1983)). The electrovalency of the aluminum-containing tetrahedra is compensated by the inclusion of cations in the crystal, for example an alkali metal or hydrogen ion. Cation exchange is possible. The spaces between the tetrahedra are occupied by water molecules prior to dehydration or calcination.

In the zeolites, it is also possible for other metals, such as B, Ga, Fe, Cr, V, As, Sb, Bi or Be or a mixture of these, instead of aluminum, to be incorporated into the lattice, or to replace the silicon by a tetravalent element such as Ge, Ti, Zr or Hf.

Depending on their structure, zeolites are divided into various groups. Thus, the zeolite structure is formed by chains of tetrahedra in the mordenite group or by sheets of tetrahedra in the chabasite group, while in the faujasite group the tetrahedra are arranged to form polyhedra, for example in the form of a cubooctahedron, which consists of 4-membered rings and 6-membered rings. Depending on the bonding of the cubooctahedra, which results in cavities and pores of different sizes, a distinction is made among zeolites of the A, L, X or Y type.

Catalysts which are suitable for the novel process are zeolites of the mordenite group or fine-pored zeolites of the erionite or chabasite type or zeolites of the faujasite type, for example Y, X or L zeolites. This group of zeolites also includes the ultrastable zeolites of the faujasite type, i.e. dealuminized zeolites. Processes for the preparation of such zeolites are described in Catalysis by Zeolites, Volume 5, from Studies in Surface Science and Catalysis, ed. B. Imelik et al., Elsevier Scientific Publishing Comp. 1980, page 203, and Crystal Structures of Ultra-stable Faujasites, Advances in Chemistry Series No. 101, American Chemical Society, Washington D.C., page 226 et seq. (1971) and in U.S. Pat. No. 4,512,961.

Zeolites of the pentasil type are particularly advantageously used. These possess, as a common basic building block, a 5-membered ring consisting of $SiO_4$ tetrahedra. They have a high $SiO_2/Al_2O_3$ ratio and pore sizes which are between those of the zeolites of type A and those of type X or Y.

These zeolites may have different chemical compositions. They are aluminosilicate, borosilicate, iron silicate, beryllium silicate, gallium silicate, chromium silicate, arsenosilicate, antimony silicate and bismuth silicate zeolites or mixtures of these, as well as aluminogermanate, borogermanate, gallium germanate and iron germanate zeolites or mixtures of these. The aluminosilicate, borosilicate and iron silicate zeolites of the pentasil type are particularly suitable for the novel process. The aluminosilicate zeolite is prepared, for example, from an aluminum compound, preferably $Al(OH)_3$ or $Al_2(SO_4)_3$, and a silicon component, preferably finely divided silica, in aqueous amine solution, in particular in a polyamine, such as 1,6-hexanediamine or 1,3-propanediamine or triethylenetetramine solution, with or, in particular, without the addition of an alkali metal or alkaline earth metal, at from 100° to 220° C. under autogenous pressure. They also include the isotactic zeolites according to European Patents 34,727 and 46,504. Depending on the amounts of starting materials chosen, the aluminosilicate zeolites obtained have an $SiO_2/Al_2O_3$ ratio of from 10 to 40,000. Aluminosilicate zeolites of this type can also be synthesized in an ether medium, such as diethylene glycol dimethyl ether, in an alcoholic medium, such as methanol or butane-1,4-diol, or in water.

The borosilicate zeolite is synthesized, for example, at from 90° to 200° C. under autogenous pressure by reacting a boron compound, e.g. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali metal or alkaline earth metal. These also include the abovementioned isotactic zeolites containing boron. Borosilicate zeolites may likewise be prepared in ether solution, e.g. diethylene glycol dimethyl ether, or in alcoholic solution, e.g. hexane-1,6-diol, instead of in aqueous amine solution.

The iron silicate zeolite is obtained, for example, from an iron compound, preferably $Fe_2(SO_4)_3$, and a silicon compound, preferably finely divided silica, in aqueous amine solution, in particular 1,6-hexanediamine, with or without the addition of an alkali metal or alkaline earth metal, at from 100° to 220° C. under autogenous pressure.

The silicon-rich zeolites which can be used ($SiO_2/Al_2O_3 \geq 10$) include the ZSM types ferrierite, NU-1 and Silicalite ® molecular sieves, i.e. silica polymorphs.

The aluminosilicate, borosilicate and iron silicate zeolites thus prepared can be isolated, dried at from 100° to 160° C., preferably 110° C., and calcined at from 450° to 550° C., preferably 500° C., and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 90:5, preferably 75:25, silica, preferably finely divided $SiO_2$, mixtures of finely divided $SiO_2$ and finely divided $Al_2O_3$, $TiO_2$, $ZrO_2$ and clay. After the molding procedure, the extrudates or pellets are dried at 110° C. for 16 hours and calcined at 500° C. for 16 hours.

Advantageous catalysts are also obtained if the aluminosilicate or borosilicate zeolite isolated is molded directly after drying and not subjected to calcination until after the molding procedure. The aluminosilicate and borosilicate zeolites prepared can be used in pure form, without a binder, as extrudates or pellets, for example ethylcellulose, stearic acid, potato starch, formic acid, oxalic acid, acetic acid, nitric acid, ammonia, amines, silicoesters and graphite or mixtures of these being used as extrusion assistants or peptizing assistants.

If, because of its method of preparation, the zeolite is not in the catalytically active, acidic H form but, for example, in the Na form, the latter can be converted completely or partially to the desired H form by ion exchange, for example with ammonium ions, and subsequent calcination, or by treatment with an acid.

If deactivation due to coking occurs when the zeolite catalysts are used according to the invention, it is advisable to regenerate the zeolites by burning off the coke deposit with air or with an air/N₂ mixture at from 400° to 550° C., preferably 550° C. As a result, the zeolites regain their initial activity.

By partial precoking, it is possible to adjust the activity of the catalyst to obtain optimum selectivity with respect to the desired reaction product.

To obtain very high selectivity, high conversion and a long catalyst life, it may be advantageous to modify the zeolites. In a suitable method of modifying catalysts, for example, the unmolded or molded zeolites are doped with metal salts by ion exchange or by impregnation. The metals used are alkali metals, such as Li, Cs or K, alkaline earth metals, such as Mg, Ca or Sr, metals of main groups 3, 4 and 5, such as Al, Ga, Ge, Sn, Pb or Bi, transition metals of subgroups 4–8, such as Ti, Zr, V, Nb, Cr, Mo, W, Mn, Re, Fe, Ru, Os, Co, Rh, Ir, Ni, Pd or Pt, transition metals of subgroups 1 and 2, such as Cu, Ag or Zn, and rare earth metals, such as La, Ce, Pr, Nd, Er, Yb and U.

Advantageously, doping is carried out, for example, as follows: the molded zeolite is initially taken in a riser tube, and, for example, an aqueous or ammoniacal solution of a halide or of a nitrate of the metals described above is passed over at from 20° to 100° C. Ion exchange of this type may be carried out, for example, on the hydrogen, ammonium or alkali metal form of the zeolite. In another possible method of applying metals to the zeolite, the zeolite material is impregnated, for example with a halide, a nitrate or an oxide of the metals described above, in aqueous, alcoholic or ammoniacal solution. Ion exchange as well as impregnation are followed by one or more drying procedures and, if desired, repeated calcination.

In a possible embodiment, $Cu(NO_3)_2.3H_2O$ or $Ni(NO_3)_2.6H_2O$ or $Ce(NO_3)_3.6H_2O$ or $La(NO_3)_2.6H_2O$ or $Cs_2CO_3$ is dissolved in water. This solution is used to impregnate the molded or unmolded zeolite for a certain time, i.e. about 30 minutes. Any supernatant solution is freed from water in a rotary evaporator. Thereafter, the impregnated zeolite is dried at about 150° C. and calcined at about 550° C. This impregnation process can be carried out several times in succession in order to obtain the desired metal content.

It is also possible to prepare an aqueous $Ni(NO_3)_2$ solution or ammoniacal $Pd(NO_3)_2$ solution and to suspend the pure powdered zeolite therein at from 40° to 100° C. for about 24 hours, while stirring. After being filtered off, dried at about 150° C. and calcined at about 500° C., the zeolite material thus obtained can be further processed with or without a binder to give extrudates, pellets fluidizable material.

Ion exchange of the zeolite in the H form, ammonium form or alkali metal form can be carried out as follows: the zeolite, in the form of extrudates or pellets, is initially taken in a column and, for example, an aqueous $Ni(NO_3)_2$ solution or ammoniacal $Pd(NO_3)_2$ solution is circulated over the said zeolite at slightly elevated temperatures at from 30° to 80° C. for from 15 to 20 hours. Thereafter, the product is washed thoroughly with water, dried at about 150° C. and calcined at about 550° C. In the case of some metal-doped zeolites, for example Pd-, Cu- or Ni-doped zeolites, aftertreatment with hydrogen is advantageous.

In another possible method of modification, the molded or unmolded zeolite material is subjected to treatment with an acid, such as hydrochloric acid, hydrofluoric acid or phosphoric acid and/or steam. An advantageous procedure comprises, for example, treating zeolites in powder form with 1N phosphoric acid for 1 hour at 80° C. The treatment is followed by washing with water, drying at 110° C. for 16 hours and calcination at 500° C. for 20 hours. In another procedure, zeolites, before or after being molded with a binder, are treated with 3–25, in particular 12–20, % strength by weight aqueous hydrochloric acid, for example for from 1 to 3 hours at from 60° to 80° C. The zeolite thus treated is then washed with water, dried, and calcined at from 400° to 500° C.

In a particular embodiment of the acid treatment, the zeolite material, before being molded, is treated at elevated temperatures with hydrofluoric acid, which is generally used in the form of from 0.001 to 2N, preferably from 0.05 to 0.5N, hydrofluoric acid, for example by refluxing for about 0.5–5, preferably 1–3, hours. After the zeolite material has been isolated, for example by filtering it off and washing it thoroughly, it is advantageously dried at from 100° to 160° C. and calcined at about 450°–600° C. In another preferred embodiment of the acid treatment, the zeolite material is molded with a binder and then treated at elevated temperatures, advantageously from 50° to 90° C., preferably from 60° to 80° C., for from 0.5 to 5 hours with from 12 to 20% strength by weight hydrochloric acid. The zeolite material is then washed thoroughly and advantageously dried at from 100° to 160° C. and calcined at about 450°–600° C. An HF treatment can also be followed by an HCl treatment.

In another procedure, zeolites can be modified by applying phosphorus compounds, such as trimethylphosphate, trimethylphosphine or primary, secondary or tertiary sodium phosphate. In this procedure, the zeolites in the form of extrudates, pellets or fluidizable material are impregnated, for example with aqueous $NaH_2PO_4$ solution, dried at 110° C. and calcined at 500° C.

If deactivation due to coking occurs when the zeolite catalysts or the other suitable catalysts are used according to the invention, it is advisable to regenerate the said catalysts by burning off the coke deposit with air or with an air/N₂ mixture at from 400° to 550° C., preferably 500° C. As a result, the zeolites regain their initial activity.

By partial precoking, it is possible to adjust the activity of the catalyst to obtain optimum selectivity with respect to the desired reaction product.

Further catalysts for the novel process are phosphates, in particular aluminum phosphates, silicon aluminum phosphates, silicon iron aluminum phosphates, boron aluminum phosphates, iron aluminum phosphates, cerium phosphates, zirconium phosphates, boron phosphates, iron phosphates, strontium phosphates or mixtures of these.

In particular, aluminum phosphates synthesized under hydrothermal conditions are used as aluminum phosphate catalysts for the novel process. Examples of suitable aluminum phosphates are APO-5, APO-9, APO-11, APO-12, APO-14, APO-21, APO-25, APO-31 and APO-33.

For example, AlPO₄-5 (APO-5) is synthesized by homogeneously mixing orthophosphoric acid with pseudoboehmite (Catapal SB R) in water; tetrapropylammonium hydroxide is added to this mixture, after which reaction is carried out at about 150° C. for from 20 to 60 hours under autogenous pressure in an autoclave. The AlPO₄ filtered off is dried at from 100° to 160° C. and calcined at from 450° to 550° C.

AlPO$_4$-9 (APO-9) is likewise synthesized from orthophosphoric acid and pseudoboehmite, but in aqueous DABCO solution (1,4-diazabicyclo(2.2.2)octane) at about 200° C. under autogenous pressure in the course of from 200 to 400 hours. If ethylenediamine is used instead of DABCO solution, APO-12 is obtained.

AlPO$_4$-21 (APO-21) is synthesized from orthophosphoric acid and pseudoboehmite in aqueous pyrrolidone solution at from 150° to 200° C. under autogenous pressure in the course of from 50 to 200 hours.

Known silicon aluminum phosphates, such as SAPO-5, SAPO-11, SAPO-31 and SAPO-34, can also be used for the novel process. These compounds are prepared by crystallization from an aqueous mixture at from 100° to 250° C. under autogenous pressure in the course of from 2 hours to 2 weeks, the reaction mixture of a silicon, aluminum and phosphorus component being reacted in aqueous organic amine solutions.

For example, SAPO-5 is obtained by mixing SiO$_2$, suspended in aqueous tetrapropylammonium hydroxide solution, with an aqueous suspension of pseudoboehmite and orthophosphoric acid, followed by reaction at from 150° to 200° C. in the course of from 20 to 200 hours under autogenous pressure in a stirred autoclave. The powder filtered off is dried at from 110° to 160° C. and calcined at from 450° to 550° C.

Other suitable silicon aluminum phosphates are ZYT-5, ZYT-6, ZYT-7, ZYT-9, ZYT-11 and ZYT-12.

Precipitated aluminum phosphates can also be used as phosphate catalysts in the process. For example, an aluminum phosphate of this type is prepared by dissolving 92 g of diammonium hydrogen phosphate in 700 ml of water. 260 g of Al(NO$_3$)$_3$.H$_2$O in 700 ml of water are added dropwise to this solution in the course of 2 hours. The pH is kept at 8 by simultaneously adding 25% strength NH$_3$ solution. The resulting precipitate is stirred for a further 12 hours, after which it is filtered off under suction, washed thoroughly and dried at 60° C. for 16 hours.

Boron phosphates as catalysts for the novel process can be prepared, for example, by mixing and kneading concentrated boric acid and phosphoric acid and then drying and calcining the product in an inert gas, air or steam atmosphere at from 250° to 650° C., preferably from 300° to 500° C.

Modifying components, as described above in the case of the zeolites, can be applied to these phosphates by impregnation (immersion and spraying on) or, in some cases, also by ion exchange. As in the case of the zeolite catalysts, modification with acids can also be carried out.

Examples of suitable acid, solid catalysts include the acidic oxides of elements of main groups III and IV and of subgroups IV to VI of the Periodic Table, in particular oxides such as silica in the form of silica gel, kieselguhr or quartz, as well as titanium dioxide, zirconium dioxide, vanadium oxides, niobium oxides, boron oxides, aluminas, chromium oxides, molybdenum oxides, tungsten oxides, pumice or mixtures of these oxides. These oxides too can be doped by applying modifying components, as described above in the case of the zeolite catalysts. The treatment with acids, as described above for the zeolite catalysts, is also a possible method of modification.

The catalysts described here may be used alternatively as 2-4 mm extrudates or as pellets of 3-5 mm diameter or as chips having particle sizes of from 0.1 to 0.5 mm or as a fluidized catalyst.

The process according to the invention can be carried out under the following reaction conditions:

The molar ratio of starting material II or III to NH$_3$ can be from 1:1 to 1:10, in particular from 1:1 to 1:5.

The reaction is advantageously carried out in the gas phase, for example at from 100° to 500° C., advantageously from 150° to 450° C., in particular from 200° to 400° C., as a rule under from 0.1 to 100, in particular from 0.5 to 10, bar.

In the gas phase, the weight hourly space velocity (WHSV) is advantageously chosen as from 0.1 to 20, in particular from 1 to 10, g of starting material per g of catalyst per hour.

The reactions in the gas phase can be carried out in a fixed bed or fluidized bed.

It is also possible to carry out the reaction in the liquid phase (suspension, trickle-bed or liquid phase procedure) at from 50° to 200° C.

The process can be carried out continuously or batchwise.

Sparingly volatile or solid starting materials are used in dissolved form, for example in solution in tetrahydrofuran, toluene or petroleum ether. In general, the starting material can be diluted with such a solvent or with an inert gas, such as N$_2$, Ar or steam. It is also possible to carry out the reaction in the presence of O$_2$.

After the reaction, the products obtained are isolated from the reaction mixture by a conventional method, for example by distillation; unconverted starting materials are, if required, recycled to the reaction.

The substituted pyridines obtainable by the novel process are versatile intermediates for the preparation of dyes, drugs and pesticides and are useful solvents. Possible uses are described in Chem. Techn. 19 (9) (1967), 528–537 and Ullmanns Enzyklopädie der technischen Chemie, Volume 14, page 467.

EXAMPLES 1-29

The reactions in the gas phase are carried out under isothermal conditions in a tubular reactor (coil, 0.6 cm internal diameter, 90 cm length) in the course of not less than 6 hours. The reaction products are isolated by a conventional method and are characterized. Quantitative determination of the reaction products and of the starting materials is effected by a known method of gas chromatography.

The following catalysts are used:

Catalyst A

The borosilicate zeolite of the pentasil type is prepared in a hydrothermal synthesis from 640 g of finely divided SiO$_2$, 122 g of H$_3$BO$_3$ and 8,000 g of an aqueous 1,6-hexanediamine solution (50:50% by weight mixture) at 170° C. under autogenous pressure in a stirred autoclave. After being filtered off and washed thoroughly, the crystalline reaction product is dried at 100° C. for 24 hours and calcined at 500° C. for 24 hours. This borosilicate zeolite is composed of 94.2% by weight of SiO$_2$ and 2.3% by weight of B$_2$O$_3$.

Catalyst A is obtained by molding the borosilicate zeolite with boehmite in a weight ratio of 60:40 to give 2 mm extrudates and drying the latter at 110° C. for 16 hours and calcining them at 500° for 24 hours.

Catalyst B

An aluminosilicate zeolite of the pentasil type is prepared under hydrothermal conditions, under autogenous pressure and at 150° C., from 65 g of finely divided SiO$_2$ and 20.3 g of Al$_2$(SO$_4$)$_3$.18H$_2$O in 1 kg of an aqueous 1,6-hexanediamine solution (50:50% by weight mixture) in a stirred autoclave. After being filtered off and washed thoroughly, the crystalline reaction product is dried at 110° C. for 24 hours and calcined at 500° C. for 24 hours. This aluminosilicate zeolite contains 91.6% by weight of $SiO_2$ and 4.6% by weight of $Al_2O_3$.

Catalyst B is obtained by molding the aluminosilicate zeolite with boehmite in a weight ratio of 60:40 to give 2 mm extrudates and drying the latter at 100° C. for 16 hours and calcining them at 500° C. for 24 hours.

Catalyst C 100 g of the borosilicate zeolite used in the case of catalyst A are treated with 280 ml of 0.1N HF at 90° C. for 2 hours, filtered off and then dried at 160° C. This product is molded with amorphous aluminosilicate (25% by weight of $Al_2O_3$ and 75% by weight of $SiO_2$) in a weight ratio of 60:40 to give 2 mm extrudates, which are dried at 110° C. for 16 hours and calcined at 500° C. for 16 hours.

Catalyst D

Catalyst D is obtained by impregnating catalyst A with an aqueous $La(NO_3)_2$ solution, followed by drying at 130° C. for 2 hours and calcination at 540° C. for 2 hours. the La content is 3.2% by weight.

Catalyst E 2 mm extrudates are prepared by molding with a molding assistant, using the borosilicate zeolite powder prepared for catalyst A, and the extrudates are dried at 110° C. for 16 hours and calcined at 500° C. for 24 hours. Catalyst E is obtained by impregnating these extrudates with an aqueous $Ce(NO_3)_3$ solution, drying them at 130° C. for 2 hours and calcining them at 540° C. for 2 hours. The Ce content is 2.5% by weight.

Catalyst F

Catalyst F is obtained in the same way as catalyst E, except that $Co(NO_3)_2$ solution is used instead of $Ce(NO_3)_3$. The Co content is 3.2% by weight.

Catalyst G

Catalyst G is obtained by impregnating catalyst B with an aqueous $La(NO_3)_3$ solution, drying the product at 130° C. for 2 hours and calcining it at 540° C. for 2 hours. The La content is 3.2% by weight.

Catalyst H

Commercial NaY zeolite is molded with boehmite in a weight ratio of 60:40 to give 2 mm extrudates, which are dried at 110° C. for 16 hours and calcined at 540° C. for 24 hours. These extrudates are subjected to ion exchange with 20% strength aqueous $La(NO_3)_2$ solution at 80° C. for 2 hours. After drying at 110° C. and calcination at 500° C., the La content should be 7.1% by weight and the Na content should be 1.1% by weight. After intermediate calcination, the ion exchange can be repeated until the above La and Na contents are obtained.

Catalyst I 660 g of silica sol (30% by weight of $SiO_2$) are mixed with 567 g of 20% strength by weight aqueous tetrapropylammonium hydroxide solution and reacted in an autoclave at 200° C. for 72 hours. After the mother liquor has been separated off, the product is dried at 120° C. and calcined at 500° C. for 16 hours. The X-ray diffraction pattern typical of Silicalit ® is obtained. This Silicalit is molded with finely divided $SiO_2$ in a weight ratio of 70:30 to give 2 mm extrudates, which are subjected to ion exchange with a 20% strength $Na_4Cl$ solution at 80° C. in a column. Thereafter, the product is washed thoroughly with water, dried at 110° C. and calcined at 500° C. for 5 hours. The Na content of the Silicalite after this procedure is 0.015% by weight. The ion exchange can be repeated in order to obtain this Na content.

Catalyst J

The iron silicate zeolite of the pentasil type is synthesized under hydrothermal conditions, under autogenous pressure and at 165° C., from 273 g of water-glass, dissolved in 253 g of an aqueous 1,6-hexanediamine solution (50:50% by weight mixture), and 31 g of iron sulfate, dissolved in 21 g of 96% strength sulfuric acid and 425 g of water, in a stirred autoclave in the course of 4 days. The zeolite is filtered off, washed thoroughly, dried at 110° C. for 24 hours and calcined at 500° C. for 24 hours. The iron silicate zeolite obtained has an $SiO_2/Fe_2O_3$ ratio of 17.7 and an $Na_2O$ content of 1.2% by weight. The catalyst is extruded with finely divided $SiO_2$ in a weight ratio of 80:20 to give 2.5 mm extrudates, which are dried at 110° C. for 16 hours and calcined at 500° C. for 24 hours.

Catalyst K $AlPO_4$-9 (APO-9) is synthesized by dissolving 200 g of 98% strength phosphoric acid, and suspending 136 g of boehmite, in 400 g of water, adding an aqueous solution of 112 g of diazabicyco(2.2.2)octane (DABCO) and 320 g of $H_2O$, and reacting this mixture in a stirred autoclave at 200° C. in the course of 336 hours under autogenous pressure. After it has been filtered off, the crystalline material is dried at 120° C. and calcined at 500° C. for 16 hours. The $AlPO_4$-9 synthesized in this manner contains 49.0% by weight of $P_2O_5$ and 37.1% of $Al_2O_3$. This material is molded with an extrusion assistant to give 3 mm extrudates, which are dried repeatedly at 120° C. and calcined at 500° C. for 6 hours.

Catalyst L $AlPO_4$-5 (APO-5) is synthesized by stirring together 200 g of 98% strength phosphoric acid, dissolved in 325 g of $H_2O$, 136 g of boehmite and 678 g of 30% strength tetrapropylammonium hydroxide and then carrying out the reaction at 150° C. under autogenous pressure in the course of 43 hours. The product dried at 120° C. and calcined at 500° C. for 16 hours contains 46.5% by weight of $P_2O_5$ and 45.5% by weight of $Al_2O_3$. This $AlPO_4$-5 is molded with boehmite in a weight ratio of 60:40 to give 2 mm extrudates, which are dried at 110° C. and calcined at 500° C. for 16 hours.

Catalyst M

Silicon aluminum phosphate-5 (SAPO-5) is prepared from a mixture of 200 g of 98% strength phosphoric acid, 136 g of boehmite, 60 g of 30% strength silica gel, 287 g of tripropylamine and 587 g of $H_2O$. This mixture is reacted at 150° C. in the course of 168 hours under autogenous pressure. After filtration, the crystalline product is dried at 120° C. and calcined at 500° C. SAPO-5 contains 49.8% by weight of $P_2O_5$, 33.0% by weight of $Al_2O_3$ and 6.2% by weight of $SiO_2$. SAPO-5 is molded with an extrusion assistant to give 3 mm extrudates, which are dried at 120° C. and calcined at 500° C.

Catalyst N $BPO_4$ is prepared by combining 49 g of $H_3BO_3$ with 117 g of $H_3PO_4$ (75% strength), in a kneader, evaporating excess water and molding the reaction product to give 3 mm extrudates. These extrudates are dried at 100° C. and calcined at 350° C. Catalyst N contains 8.77% by weight of B and 28.3% by weight of P.

Catalyst O $CePO_4$ is obtained by precipitation from 52 g of $Ce(NO_3)_3.6H_2O$ and 56 g of $NaH_2PO_4.2H_2O$. After filtration, the material is converted to extrudates, which are dried at 120° C. and calcined at 450° C. Catalyst O contains 47.1% by weight of Ce and 12.7% by weight of P.

Catalyst P

Catalyst P is a precipitated aluminum phosphate which is obtained by precipitation from Al(NO$_3$)$_3$/H$_3$PO$_4$ solution with NH$_3$ at pH 6-7. The precipitate is filtered off, dried at 110° C. and calcined at 500° C. Catalyst P contains 28.5% by weight of Al and 13.2% by weight of P.

Catalyst Q

Commercial zirconium phosphate (CZP 100 ®) is molded with molding assistants to give 2 mm extrudates, which are dried at 110° C. and calcined at 500° C. for 16 hours.

Catalyst R

SiO$_2$ commercially available under the name D-11-10 ®.

Catalyst S 100 g of SiO$_2$ extrudates (D 11-10) are treated with 280 ml of 0.1N HF and 80 ml of H$_2$O under reflux for 1 hour. Thereafter, the material is washed neutral, dried at 100° C. and calcined at 500° C. for 5 hours.

Catalyst T

Al$_2$O$_3$ commercially available under the name D 10-10 ®.

Catalyst U

TiO$_2$ P 25 ® is molded to give 2 mm extrudates, which are dried at 110° C. and calcined at 500° C. for 16 hours.

Catalyst V

Catalyst V is obtained by treating catalyst U as described for catalyst S.

Catalyst W 200 g of catalyst U are treated with 600 ml of 15% strength HCl at 80° C. for 1 hour. Thereafter, the material is washed Cl-free, dried at 100° C. and calcined at 600° C. for 1 hour.

Catalyst X (comparison catalyst)

Commercial MgO in pellet form.

The experimental results obtained using these catalysts and the experimental conditions are described in Tables 1 and 2.

Tables 1 and 2 show that the zeolite catalysts are particularly advantageous for the process according to the invention.

Frequent byproducts in these reactions are methylpyridines and ethylpyridines.

TABLE 1

Pyridine from 2-methoxy-2,3-dihydro-4H-pryan and NH$_3$ (molar ratio 1:3)

| Example | 1 | 2 | 3 | 4 | 5 | 6 | 7 | 8 | 9 | 10 | 11 |
|---|---|---|---|---|---|---|---|---|---|---|---|
| Catalyst | A | B | C | E | H | I | J | K | L | M | N |
| Temperature °C. | 400 | 400 | 400 | 400 | 400 | 400 | 400 | 400 | 400 | 400 | 400 |
| WHSV h$^{-1}$ | 3 | 3 | 3 | 3 | 3 | 3 | 3 | 3 | 3 | 3 | 3 |
| Conversion % | 100 | 100 | 100 | 100 | 100 | 100 | 100 | 100 | 100 | 100 | 94.9 |
| Selectivity % Pyridine | 93.1 | 93.9 | 95.3 | 76.8 | 78.6 | 77.4 | 80.3 | 79.5 | 72.1 | 84.6 | 70.3 |

| Example | 12 | 13 | 14 | 15 | 16 | 17 | 18 | 19 | 20 | 21 |
|---|---|---|---|---|---|---|---|---|---|---|
| Catalyst | O | P | Q | R | S | T | U | V | W | X |
| Temperature °C. | 400 | 400 | 400 | 400 | 400 | 400 | 400 | 400 | 400 | 400 |
| WHSV h$^{-1}$ | 3 | 3 | 3 | 3 | 3 | 3 | 3 | 3 | 3 | 3 |
| Conversion % | 98.0 | 100 | 100 | 97.8 | 83.4 | 92.2 | 100 | 100 | 100 | 4.9 |
| Selectivity % Pyridine | 69.2 | 84.6 | 65.8 | 61.3 | 62.9 | 67.4 | 87.0 | 86.9 | 87.8 | 28.4 |

TABLE 2

| | Pyridine from glutaraldehyde and NH$_3$ | | | | | | | |
|---|---|---|---|---|---|---|---|---|
| Example | 22 | 23 | 24 | 25 | 26 | 27 | 28 | 29 |
| Catalyst | A | B | C | D | E | F | G | H |
| Temperature °C. | 400 | 400 | 400 | 400 | 400 | 400 | 400 | 400 |
| WHSV h$^{-1}$ | 1.0 | 0.5 | 0.5 | 0.5 | 0.5 | 0.5 | 0.5 | 0.5 |
| Conversion % | 100 | 100 | 100 | 100 | 100 | 100 | 100 | 100 |
| Selectivity % Pyridine | 84.1 | 83.0 | 88.7 | 80.1 | 78.6 | 84.9 | 75.3 | 88.5 |

(1) Based on glutaraldehyde
(2) Molar ratio of glutaraldehyde to NH$_3$ = 1:6
(3) 25% strength aqueous glutaraldehyde solution

EXAMPLES 30 AND 31

A solution of 4-phenyl-2-isopropoxydihydropyran and tetrahydrofuran in a weight ratio of 9:1 is reacted with NH$_3$ in a molar ratio of 1:32 at 400° C. and a WHSV of 2.5 h$^{-1}$ over catalyst H in an isothermal fixed-bed reactor (see preceding Examples). The conversion based on dihydropyran is 63.3% and the selectivity based on phenylpyridine is 88.9%.

Over catalyst A and under the same conditions, a conversion of 62.5% and a selectivity of 79.7% are obtained.

EXAMPLE 32

A solution of 2-ethyl-3,4-dimethyl-5-ethoxydihydropyran and tetrahydrofuran in a weight ratio of 50:50 is reacted with NH$_3$ in a molar ratio of 1:5 at 350° C. and a WHSV of 1.5 h$^{-1}$ over catalyst H in an isothermal fixed-bed reactor. The conversion based on dihydropyran is 100% and the selectivity based on ethyldimethylpyridine is 71%.

EXAMPLES 33 AND 34

A solution of 3-hexyl-2-butoxydihydropyran and tetrahydrofuran in a weight ratio of 50:50 is reacted with $NH_3$ in a molar ratio of 1:3 at 350° C. and a WHSV of 2 $h^{-1}$ over catalyst A in an isothermal fixed-bed reactor. The conversion based on dihydropyran is 100% and the selectivity based on 3-hexylpyridine is 74.3%.

Over catalyst U and under the same conditions, a conversion of 100% and a selectivity of 78.2% are obtained.

We claim:

1. A process for the preparation of pyridine of the formula (I)

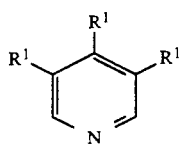

where the individual radicals $R^1$ may be identical or different and are each hydrogen or an alkyl radical of 1 to 8 carbon atoms optionally substituted by alkyl, alkoxy or carboxyl groups of 1 to 4 carbon atoms the process comprising reacting:

a) a 2-alkoxy-2,3-dihydro-4H-pyran of the formula (II)

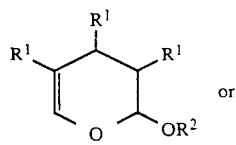

or b) a glutaraldehyde of the formula (III)

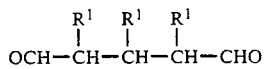

where $R^1$ has the abovementioned meanings and $R^2$ is an alkyl radical of 1 to 8 carbons which may be substituted by alkyl, alkoxy or carboxyl groups of 1 to 4 carbon atoms, with ammonia in the presence of an acidic, solid zeolite catalyst.

2. The process of claim 1, wherein the catalyst used is a zeolite of the pentasil type.

3. The process of claim 1, wherein the catalyst used is a borosilicate zeolite of the pentasil type.

4. The process of claim 1, wherein the catalyst used is an iron silicate zeolite of the pentasil type.

5. The process of claim 1, wherein the catalyst used is an aluminosilicate zeolite of the pentasil type.

6. The process of claim 1, wherein the catalyst used is an aluminosilicate zeolite of the faujasite type.

7. A process as claimed in claim 1, wherein the catalyst is treated with acids.

8. The process of claim 7, wherein the catalyst is treated with HF and/or HCl.

9. The process of claim 1, wherein the reaction is carried out in the gas phase.

10. The process of claim 1, wherein the catalyst used is an aluminosilicate or borosilicate zeolite that has been molded directly after drying and has been calcined after being molded.

11. The process of claim 7, wherein the zeolite catalyst was treated in powder form with 1N phosphoric acid for 1 hour at 80° C., washed with water, dried at 110° C. for 16 hours and calcined at 500° C. for 20 hours.

12. The process of claim 7, wherein the zeolite catalyst was treated with 3-25% strength by weight acqueous hydrochloric acid for from 1 to 3 hours at from 60° to 80° C., washed, with water, dried and calcined at from 400° to 500° C.

13. The process of claim 12, wherein the zeolite catalyst was treated with 12 to 20% strength by weight acqueous hydrochloric acid.

14. The process of claim 7, wherein the zeolite catalyst, before being molded, was treated at elevated temperatures with 0.001 to 2N hydrofluoric acid by refluxing for 1-3 hours, isolated, dried at from 100° to 160° C. and calcined at about 450° to 600° C.

15. The process of claim 7, wherein the zeolite catalyst was molded with a binder, treated at from 50° to 90° C. for from 0.5 to 5 hours with 12 to 20% strength by weight hydrochloric acid, washed thoroughly, dried at from 100° to 160° C. and calcined at about 450° to 600° C.

16. The process of claim 15, wherein the zeolite catalyst was molded with a binder at from 60° to 80° C.

* * * * *